US009265411B2

(12) United States Patent
Chen et al.

(10) Patent No.: US 9,265,411 B2

(45) Date of Patent: Feb. 23, 2016

(54) ANTERIOR SEGMENT THREE-DIMENSIONAL IMAGE PROCESSING APPARATUS, AND ANTERIOR SEGMENT THREE-DIMENSIONAL IMAGE PROCESSING METHOD

(71) Applicant: TOMEY CORPORATION, Nagoya-shi, Aichi-ken (JP)

(72) Inventors: Jinji Chen, Obu (JP); Okamoto Keiichiro, Nagoya (JP)

(73) Assignee: Tomey Corporation, Nagoya (JP)

( * ) Notice: Subject to any disclaimer, the term of this patent is extended or adjusted under 35 U.S.C. 154(b) by 0 days.

(21) Appl. No.: 14/499,062

(22) Filed: Sep. 26, 2014

(65) Prior Publication Data

US 2015/0092160 A1 Apr. 2, 2015

(30) Foreign Application Priority Data

Sep. 27, 2013 (JP) ................................ 2013-202022
Sep. 27, 2013 (JP) ................................ 2013-202023

(51) Int. Cl.

| | |
|---|---|
| ***A61B 3/14*** | (2006.01) |
| ***A61B 3/00*** | (2006.01) |
| ***A61B 3/10*** | (2006.01) |
| ***A61B 3/117*** | (2006.01) |

(52) U.S. Cl.

CPC ............... *A61B 3/0025* (2013.01); *A61B 3/102* (2013.01); *A61B 3/117* (2013.01)

(58) Field of Classification Search

CPC ...... A61B 3/0025; A61B 3/102; A61B 3/117; G06T 2207/10101; G06T 2207/30041

USPC ................................................. 351/205–221

See application file for complete search history.

(56) References Cited

PUBLICATIONS

Mishima, K., "Clinical Use of Anterior Segment OCT in Glaucoma," New Opthamology, vol. 28, No. 6, 2011, pp. 763-768 Japanese.

Mishima, K., "Clinical Use of Anterior Segment OCT in Glaucoma," New Opthamology, vol. 28, No. 6, 2011, pp. 763-768 English Translation.

*Primary Examiner* — Mahidere Sahle

(74) *Attorney, Agent, or Firm* — Patrick E. Caldwell, Esq.; The Caldwell Firm, LLC

(57) ABSTRACT

A processing apparatus is provided that receives and processes an anterior segment three-dimensional image of a subject's eye. The apparatus includes a first SS position specifying unit that accepts identification of at least three SS positions of the subject's eye, using at least two representative images from among two-dimensional tomographic images constituting the three-dimensional image, a true circle calculating unit that calculates a reference true circle passing through the at least three SS positions, and a second SS position specifying unit that identifies the SS positions in non-representative images other than the representative images, based on the reference true circle.

13 Claims, 13 Drawing Sheets

WAVELENGTH SCANNING LIGHT SOURCE
AD BOARD
COMPUTING UNIT
GALVANOMETER DRIVER
OPTICAL CONTROLLER
(ANTERIOR SEGMENT)
(SUBJECT'S EYE)
(MONITOR)

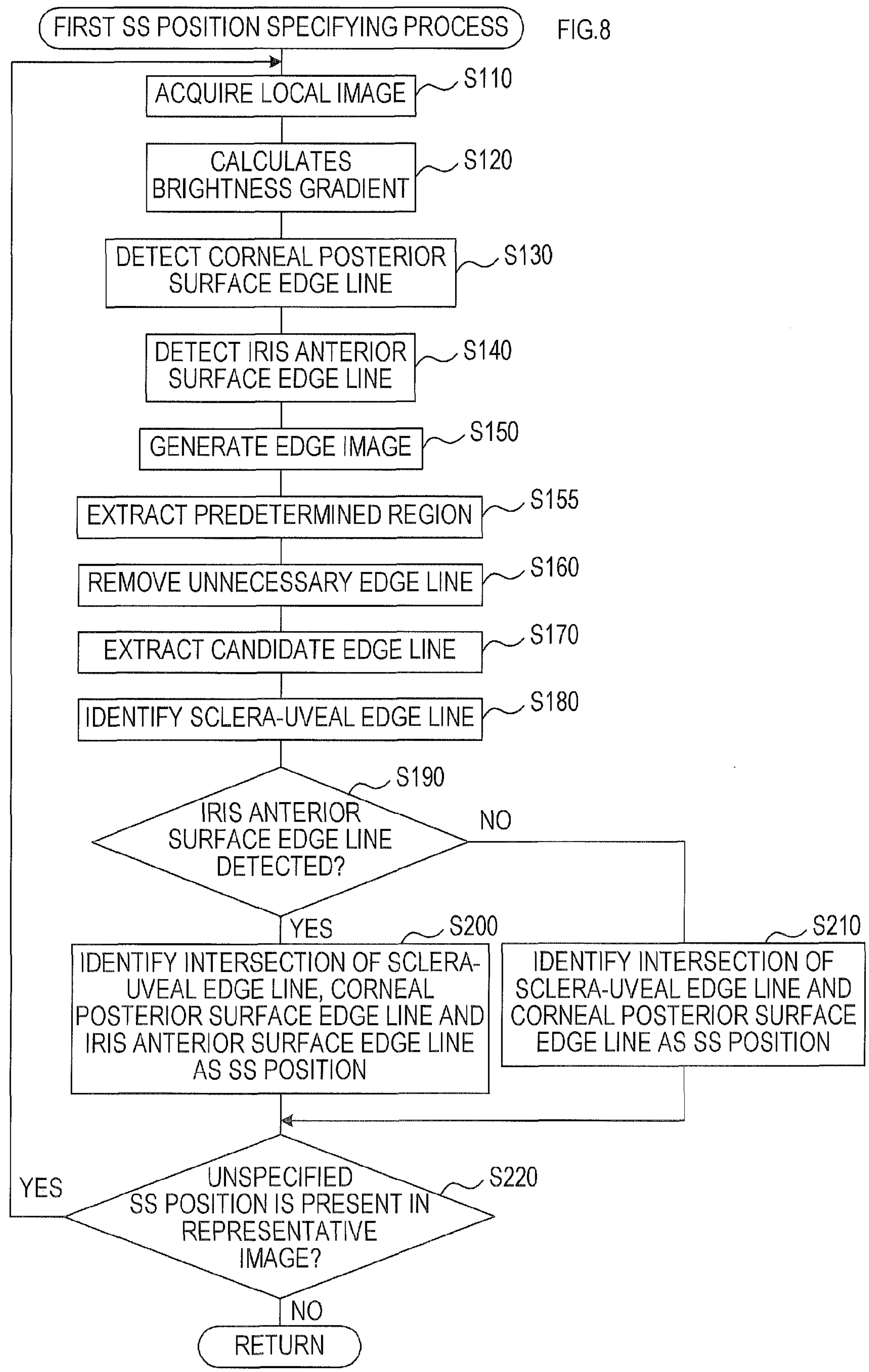
FIRST SS POSITION SPECIFYING PROCESS
FIG.8
ACQUIRE LOCAL IMAGE
S110
CALCULATES BRIGHTNESS GRADIENT
S120
DETECT CORNEAL POSTERIOR SURFACE EDGE LINE
S130
DETECT IRIS ANTERIOR SURFACE EDGE LINE
S140
GENERATE EDGE IMAGE
S150
EXTRACT PREDETERMINED REGION
S155
REMOVE UNNECESSARY EDGE LINE
S160
EXTRACT CANDIDATE EDGE LINE
S170
IDENTIFY SCLERA-UVEAL EDGE LINE
S180
IRIS ANTERIOR SURFACE EDGE LINE DETECTED?
S190
NO
YES
S200
IDENTIFY INTERSECTION OF SCLERA-UVEAL EDGE LINE, CORNEAL POSTERIOR SURFACE EDGE LINE AND IRIS ANTERIOR SURFACE EDGE LINE AS SS POSITION
S210
IDENTIFY INTERSECTION OF SCLERA-UVEAL EDGE LINE AND CORNEAL POSTERIOR SURFACE EDGE LINE AS SS POSITION
YES
UNSPECIFIED SS POSITION IS PRESENT IN REPRESENTATIVE IMAGE?
S220
NO
RETURN

LOCAL IMAGE

EDGE IMAGE

REMOVE UNNECESSARY EDGE LINE

ANTERIOR SEGMENT THREE-DIMENSIONAL IMAGE PROCESSING APPARATUS, AND ANTERIOR SEGMENT THREE-DIMENSIONAL IMAGE PROCESSING METHOD

CROSS-REFERENCE TO RELATED APPLICATIONS

This application claims the priority of Japanese Patent Application No. 2013-202022 and Japanese Patent Application No. 2013-202023 both filed Sep. 27, 2013 in the Japan Patent Office, and the entire disclosures of Japanese Patent Application No. 2013-202022 and Japanese Patent Application No. 2013-202023 are incorporated herein by reference.

BACKGROUND

The present invention relates to an anterior segment three-dimensional image processing apparatus, and an anterior segment three-dimensional image processing method.

In recent years, an optical coherence tomography (OCT) apparatus for photographing a tomographic image of an anterior segment of an eyeball of a subject (subject's eye) by means of optical coherence tomography (hereinafter "anterior segment OCT") has been provided as an inspection apparatus used for ophthalmic examination.

Specifically, the anterior segment OCT has come to be used, for example, in glaucoma clinics, largely for angle analysis in the narrow angle eye, mainly including primary closed angle diseases and primary closed angle glaucoma together with the suspected (for example, see "Application to glaucoma of anterior segment OCT: Present" written by Koichi Mishima, new ophthalmology Vol. 28 No. 6 P. 763~768 (issue June 2011)).

Generally, in the anterior segment OCT, one-dimensional scanning by a measurement light is performed on the subject's eye to acquire a two-dimensional tomographic image of one slice plane (B-scan). Further, the two-dimensional tomographic image is repeatedly acquired while shifting a scanning position of the measurement light (in other words, while changing the slice plane) on the subject's eye (C-scan) to obtain an anterior segment three-dimensional image.

As a method of scanning, there is, for example, a method called raster scan, as shown in FIG. 4A. In the raster scan, one-dimensional scanning (B-scan) along a scanning line extending in a horizontal direction is repeated while the scanning position is shifted in a vertical direction (C-scan), and thereby it is possible to obtain a two-dimensional tomographic image along each scan line, as shown in FIG. 4B.

There is also, for example, a method called radial scan, as shown in FIG. 5A. According to the radial scan, one-dimensional scanning (B-scan) along the scanning line extending in a radial direction is repeated while the scanning position is shifted in a circumferential direction (C-scan), and thereby it is possible to obtain a two-dimensional tomographic image along each scan line, as shown in FIG. 5B.

In a conventional anterior segment three-dimensional image processing apparatus, an operator inputs a scleral spur position (SS position) by pointing in a two-dimensional tomographic image of the slice plane obtained as above. Thereby, it was made possible to display an angle portion (portion where a corneal posterior surface and an iris anterior surface are in contact with each other) that is closed beyond the SS position on a chart as an iridotrabecular contact (ITC).

SUMMARY

The conventional anterior segment three-dimensional image processing apparatus is configured such that the operator inputs the SS position by pointing in each of the two-dimensional tomographic images. Therefore, even if it was possible to obtain, for example, a hundred or more of two-dimensional tomographic images by the anterior segment OCT, considerable time was required before starting creation of a chart showing an ITC. Such an apparatus was difficult to use clinically.

It is preferable to provide an anterior segment three-dimensional image processing apparatus and an anterior segment three-dimensional image processing method that can be effectively utilized clinically.

The anterior segment three-dimensional image processing apparatus of the present invention is an apparatus that inputs and processes an anterior segment three-dimensional image of a subject's eye by means of an optical coherence tomography device (anterior segment OCT), and includes a first SS position specifying unit, a true circle calculating unit, and a second SS position specifying unit.

The first SS position specifying unit accepts identification of at least three SS positions indicating a spatial coordinate position of a scleral spur of the subject's eye, using at least two representative images from among a plurality of two-dimensional tomographic images that constitute the anterior segment three-dimensional image.

The true circle calculating unit calculates a reference true circle that passes through the at least three SS positions from among the SS positions identified by the first SS position specifying unit in the anterior segment three-dimensional image.

The second SS position specifying unit identifies the SS positions in images ("non-representative images" hereinafter) other than the representative images from among the plurality of two-dimensional tomographic images, based on the reference true circle calculated by the true circle calculating unit.

According to the anterior segment three-dimensional image processing apparatus configured as above, for example, only if the operator enters a total of three SS positions in two two-dimensional tomographic images, the SS positions in all the other two-dimensional tomographic images constituting the anterior segment three-dimensional image can be automatically identified. Thus, it is possible to increase the number of processes that can be automated in the anterior segment three-dimensional image processing apparatus.

Conventionally, in each of the two-dimensional tomographic images constituting the anterior segment three-dimensional image, whereas correlation of the SS positions was unknown, the applicant of the present application, while promoting angle analysis, was able to verify and confirm a hypothesis that the SS positions are plotted on a true circle on the same plane. Therefore, by only identifying at least three SS positions and calculating a reference true circle on a space plane, it became possible to identify the remaining SS positions in the anterior segment three-dimensional image.

Therefore, according to the present invention, since at least the operator no longer needs to identify the SS positions in all the two-dimensional tomographic images, it is possible to reduce time before starting creation of a chart indicating, for example, an ITC (iridotrabecular contact). Thus, the present invention can be effectively utilized clinically in angle analysis by means of an anterior segment OCT.

The anterior segment three-dimensional image processing apparatus of the present invention can further include a determining unit and a position adjusting unit.

The determining unit determines whether or not there is a displacement of a spatial coordinate position on the plurality of two-dimensional tomographic images. For example, for each of the two-dimensional tomographic images, it is determined whether there is a displacement of the spatial coordinate position.

If it is determined by the determining unit that there is a displacement of the spatial coordinate position, the position adjusting unit adjusts the displacement of the spatial coordinate position. Specifically, the mutual spatial coordinate positions in each of the two-dimensional tomographic images are adjusted. Owing to this, it is possible to more accurately identify the SS positions.

The position adjusting unit may be configured to adjust the displacement of the spatial coordinate position based on a corneal anterior surface shape of the subject's eye in the two-dimensional tomographic image. According to this configuration, for example, as for the plurality of two-dimensional tomographic images obtained by a radial scan, by translating and rotating the spatial coordinate position on the image so as to match the position of the corneal anterior surface (corneal anterior surface curve), it is possible to suitably adjust the mutual spatial coordinate positions in each of the two-dimensional tomographic images.

The position adjusting unit may be configured to adjust the displacement of the spatial coordinate position, using alignment information indicating a displacement amount of a corneal apex of the subject's eye relative to an apparatus body of the optical coherence tomography device in the two-dimensional tomographic image. According to this configuration, during filming of the anterior segment three-dimensional image, even if there is a significant movement of the subject's eye, it is possible to correct on the image, for example, an amount displaced from a straight line on which a scanning line passes through the corneal apex. Therefore, it is possible to suitably adjust the mutual spatial coordinate positions in each of the two-dimensional tomographic images.

The true circle calculating unit may calculate a reference true circle having a diameter equal to a distance between two SS positions identified using one of the representative images, from among the at least three SS positions identified by the first SS position specifying unit. According to this configuration, only by specifying at least one SS position, in addition to the two SS positions constituting the diameter, the reference true circle on the space plane is determined. Therefore, fewer two-dimensional tomographic images (representative images) can be used to calculate the reference true circle. Thus, it is possible to further increase a process that can be automated in the anterior segment three-dimensional image processing apparatus.

The first SS position specifying unit may be configured to detect a sclera-uveal edge line showing a boundary between a sclera and a uvea in the subject's eye and a corneal posterior surface edge line showing a corneal posterior surface of the subject's eye from the representative image, and identify an intersection of the detected sclera-uveal edge line and the corneal posterior surface edge line as the SS position.

According to the above, it is possible to automate the processes, and the operator need not perform input by pointing of the SS position at all. Therefore, it is possible to significantly reduce time before starting creation of a chart showing, for example, an ITC. Thus, the apparatus of the present invention can be effectively utilized clinically in angle analysis by means of the anterior segment OCT.

The first SS position specifying unit may be configured to detect an iris anterior surface edge line showing the iris anterior surface of the subject's eye from the representative image, and identify, as the SS position, an intersection of the detected sclera-uveal edge line, corneal posterior surface edge line and iris anterior surface edge line. According to the above, for example, in a two-dimensional tomographic image having no ITC, extraction of the intersection becomes easy by using the three edge lines. Therefore, it is possible to improve identification accuracy in automatic identification of the SS position.

The present invention can be realized in various forms, such as in the form of a program for causing a computer to function as the anterior segment three-dimensional image processing apparatus described above, in the form of a storage medium storing the program, etc.

Specifically, it is a program for causing a computer to function as the first SS position specifying unit, the true circle calculating unit, and the second SS position specifying unit.

The program, by being incorporated into one or more of computers, has an effect equivalent to the effect achieved by the anterior segment three-dimensional image processing apparatus of the present invention. Also, the program may be stored in a ROM that is incorporated into a computer, a flash memory or the like and may be used after being loaded into the computer from the ROM, the flash memory or the like or may be used after being loaded to the computer via a network.

The above program may be recorded on a recording medium of any form readable by a computer. The recording medium, for example, may include a hard disk, a CD-ROM/RAM, a DVD-ROM/RAM, a semiconductor memory and the like.

The present invention may also be implemented as an anterior segment three-dimensional image processing method including: a step corresponding to the first SS position specifying unit (first SS position specifying step), a step corresponding to the true circle calculating unit (true circle calculating step), and a step of corresponding the second SS position specifying unit (second SS position specifying step). According to this method, it is possible to obtain the same effect as the effect achieved by the anterior segment three-dimensional image processing apparatus of the present invention.

BRIEF DESCRIPTION OF THE DRAWINGS

In the following, embodiments of the present invention will be described with reference to the accompanying drawings in which:

FIG. 8 is a flowchart for explaining a first SS position specifying process executed in the main process;

DETAILED DESCRIPTION OF THE PREFERRED EMBODIMENTS

The present invention is not construed as being limited in any way by the following embodiments. Furthermore, embodiments of the present invention also include modes in which a portion of the following embodiments are omitted as long as the problem can be solved. Moreover, embodiments of the present invention also include any embodiments to the extent possible without departing from the essence of the invention specified only by the language of the claims.

<First Embodiment>

An anterior segment optical coherence tomography device of a first embodiment is a device used for ophthalmic examination of an anterior segment Ec (see FIG. 1) of an eyeball of a subject (subject's eye E), such as angle analysis, corneal curvature, corneal thickness distribution, measurement of anterior chamber depth, etc., and obtains a three-dimensional image by capturing a two-dimensional tomographic image of the anterior segment Ec of the subject's eye E by optical coherence tomography (OCT). Below, this anterior segment optical coherence tomography device is referred to as "anterior segment OCT1".

Although not illustrated, an apparatus body of the anterior segment OCT1 is movably supported in an X direction (horizontal direction), a Y direction (vertical direction) and a Z direction (front-rear direction), with respect to a holding table. At a front side (subject side) of the apparatus body, a jaw receiving portion and a forehead rest portion are provided in a fixed manner with respect to the holding table. When the subject places his jaw at the jaw receiving portion and rests his forehead on the forehead rest portion, an eye of the subject (subject's eye E) is adapted to be placed in front of a test window (window through which light enters and exits) for capturing provided on a anterior surface of the apparatus body.

Figure 2:
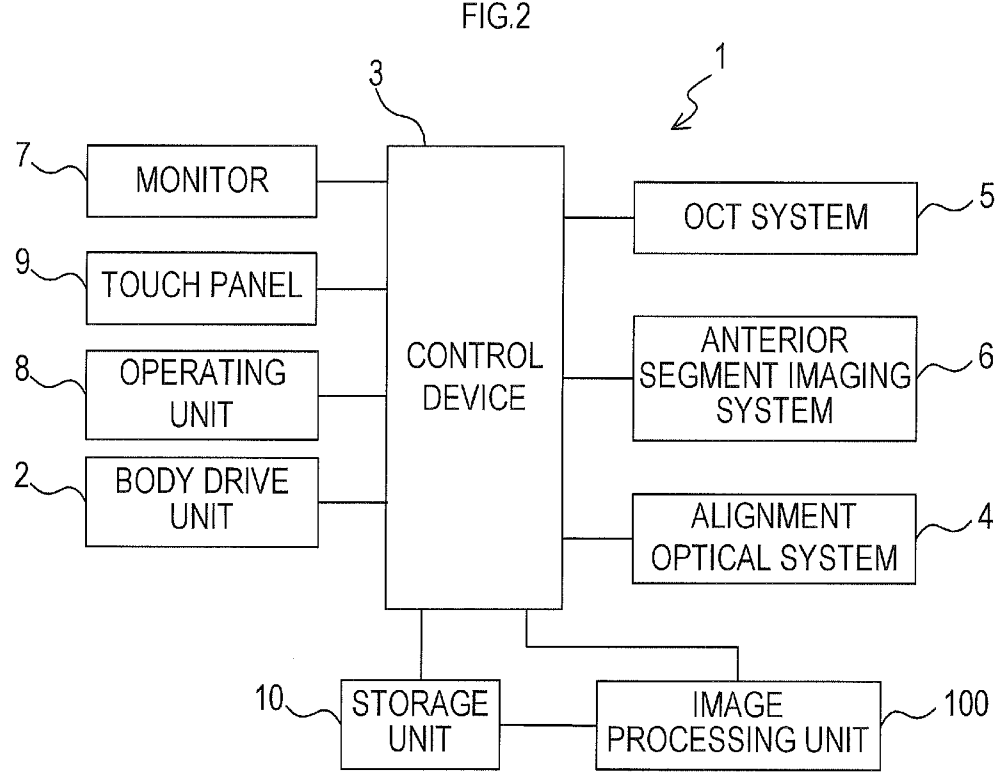
FIG. 2 is a block diagram schematically illustrating an electrical configuration of the anterior segment OCT1.

As shown in FIG. 2, in the anterior segment OCT1, a body drive unit 2 is provided for freely moving the apparatus body in the respective X, Y, and Z directions with respect to the holding table. The body drive unit 2 has a known configuration provided with an X-direction moving motor, a Y-direction moving motor, and a Z-direction moving motor, and is controlled by a control unit 3.

The apparatus body, as shown in FIG. 2, is provided with the control unit 3, an alignment optical system 4, an OCT system 5, an anterior segment imaging system 6, etc. The control unit 3 contains a microcomputer with a CPU, a memory, etc., and performs overall control. The OCT system 5 acquires a three-dimensional image (hereinafter "anterior segment three-dimensional image") of the anterior segment Ec comprising more than one two-dimensional tomographic images. The anterior segment imaging system 6 takes a front image of the subject's eye E.

Furthermore, the apparatus body is provided with a monitor 7 and an operating unit 8. The monitor 7 is placed on a rear side (operator side), and displays the front image P (see FIG. 1), etc. of the subject's eye E. The operating unit 8 is an interface for an operator to perform various operations. The operating unit 8 may include a measurement start switch, a measurement region designating switch, a keyboard, a mouse, etc., although not shown.

In FIG. 2, a touch panel 9 is shown as a component separate from the operating unit 8. The touch panel 9 may be included in the operating unit 8. The touch panel 9 may be arranged integrally with a screen of the monitor 7. To the control unit 3, a storage unit 10 and an image processing unit 100 (main part of the anterior segment three-dimensional image processing apparatus) are connected.

The storage unit 10 can be a device that can store data on a computer readable recording medium, such as a CD-ROM/RAM, a DVD-ROM/RAM, a hard disk, a semiconductor memory, etc. The storage unit 10 stores image data, etc. of the anterior segment three-dimensional image that is taken. The image processing unit 100 performs image processing, etc. of the stored data.

The OCT system 5 is a system for obtaining an anterior segment three-dimensional image by means of optical coherence tomography. In the present embodiment, a Fourier domain (optical frequency sweep) method is employed that uses a wavelength scanning light source 11 (see FIG. 1) that is operated by varying a wavelength over time.

Figure 1:
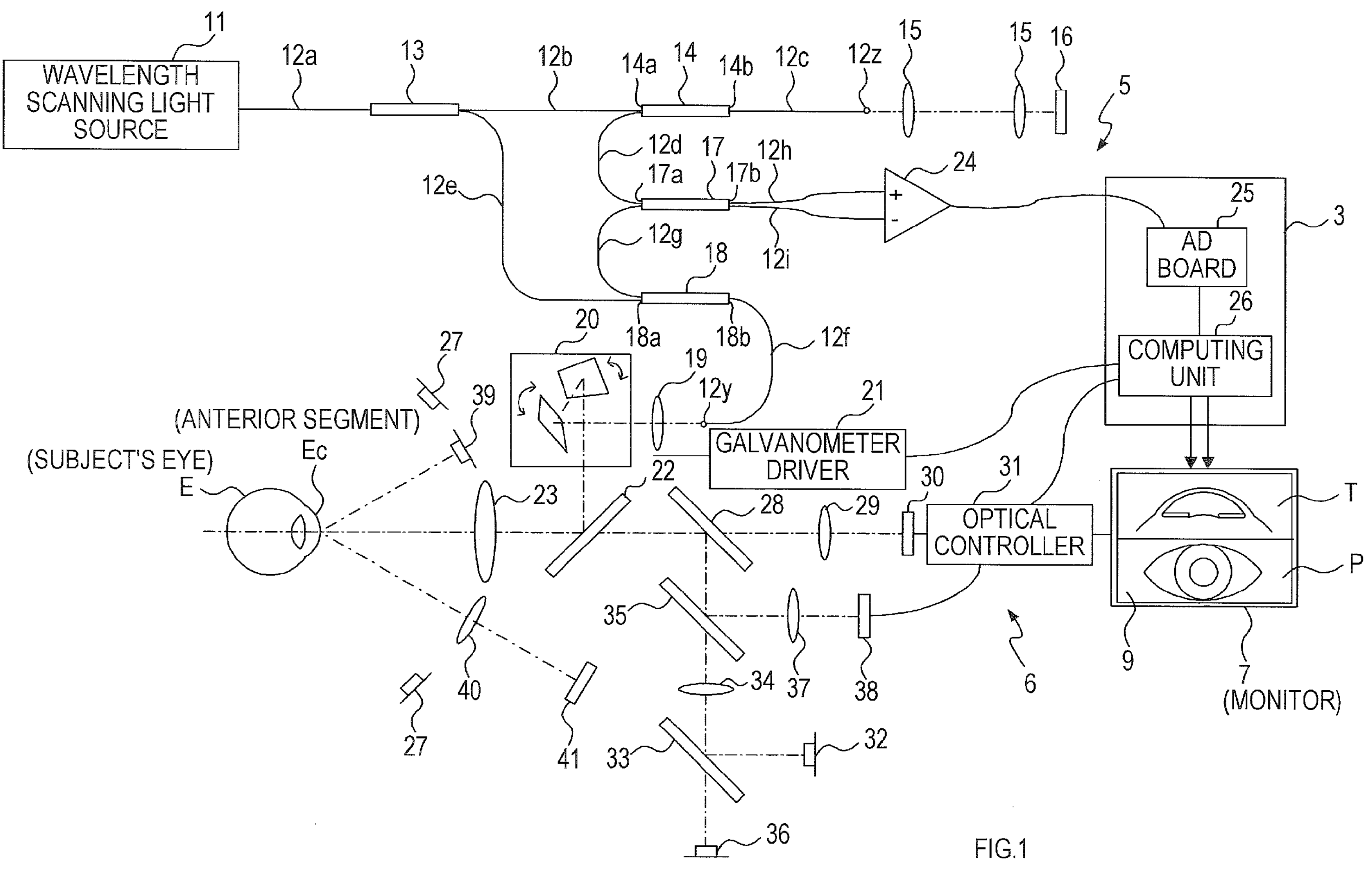
FIG. 1 is block diagram illustrating a configuration of an optical system of an anterior segment OCT1.

For example, as shown in FIG. 1, light output from the wavelength scanning light source 11 is input to a first fiber coupler 13 through an optical fiber 12*a*. In the first fiber coupler 13, the light is branched into a reference light and a measurement light, for example, in a ratio of 1:99, and is output from the first fiber coupler 13. The reference light is input to an input/output section 14*a* of a first circulator 14 through an optical fiber 12*b*. Further, the reference light, from an input/output section 14*b* of the first circulator 14 through an optical fiber 12*c*, is output from an end 12*z* of an optical fiber 12*c*, and passes through more than one collimator lens 15 to enter a reference mirror 16.

The reference light reflected by the reference mirror 16 is again input to the end 12*z* of the optical fiber 12*c* through the more than one collimator lens 15, and is input to the input/output section 14*b* of the first circulator 14 through the optical fiber 12*c*. The reference light is output from the input/output section 14*a* of the first circulator 14, and is input to a first input unit 17*a* of a second fiber coupler 17 through an optical fiber 12*d*.

On the other hand, the measurement light output from the first fiber coupler 13 is input to an input/output section 18*a* of a second circulator 18 through an optical fiber 12*e*. Further, the measurement light passes through the optical fiber 12*f* from an input/output section 18*b* of the second circulator 18 to be output from an end 12*y* of an optical fiber 12*f*.

The measurement light output from the end 12*y* of the optical fiber 12*f* is input to a galvanometer scanner 20 through a collimator lens 19. The galvanometer scanner 20 is intended for scanning the measurement light, and is driven by a galvanometer driver 21.

The measurement light output from the galvanometer scanner 20 is reflected at an angle of 90 degrees by a hot mirror 22 that reflects light on a long wavelength side and transmits light on a short wavelength side, and is emitted from an inspection window through an objective lens 23 to enter the subject's eye E.

The measurement light entering the subject's eye E is reflected on each tissue portion (cornea, bunch, iris, lens, uvea, sclera, etc.) of the anterior segment Ec, and the reflected light enters the apparatus body from the inspection window. Particularly, contrary to the above, the reflected light is input to the end 12*y* of the optical fiber 12*f* sequentially through the objective lens 23, the hot mirror 22, the galvanometer scanner 20, and the collimator lens 19.

Then, the reflected light is input to the input/output section 18*b* of the second circulator 18 through the optical fiber 12*f*, is output from the input/output section 18*a* of the second circulator 18, and is input to the first input section 17*a* of the second fiber coupler 17 through an optical fiber 12*g*.

In this second fiber coupler 17, the reflected light from the anterior segment Ec and the reference light input through the optical fiber 12*d* are combined, for example, in a ratio of 50:50, and the signal is input to a detector 24 via optical fibers 12*h*, 12*i*.

In the detector 24, interference of each wavelength is measured, and the measured interference signal is input to an AD board 25 provided in the control unit 3. Moreover, in a computing unit 26 provided in the control unit 3, a process such as a Fourier transform of the interference signal is performed, and thereby a tomographic image (two-dimensional tomographic image) of the anterior segment Ec along a scan line is obtained.

At this time, a scan pattern of the measurement light by the galvanometer scanner 20, in other words, a direction of the scan line (B-scan), is adapted to be set in the control unit 3. The galvanometer driver 21 is adapted to control the galvanometer scanner 20 in accordance with a command signal from the control unit 3 (computing unit 26).

Image data of the two-dimensional tomographic image thus obtained is stored in the storage unit 10. The image data of the two-dimensional tomographic image includes at least information indicating the brightness of each pixel. Also, as is shown schematically in FIG. 1, the tomographic image T can be displayed on the monitor 7.

The anterior segment imaging system 6 includes illumination sources 27, 27, the objective lens 23, the hot mirror 22, a cold mirror 28, an imaging lens 29, a CCD camera 30, and an optical controller 31. The illumination sources 27, 27 are adapted to irradiate illumination light in a visible light region in front of the subject's eye E.

The reflected light from the subject's eye E is input to the CCD camera 30 through the objective lens 23, the hot mirror 22, the cold mirror 28, and the imaging lens 29 from the inspection window. Owing to this, the front image P of the subject's eye E is taken. On the front image P that was taken, an image process is performed by the optical controller 31 and is displayed on the monitor 7.

The alignment optical system 4 includes a fixation lamp optical system, an XY direction position detecting system, and a Z-direction position detecting system. The fixation light optical system is configured to prevent the eyeball (subject's eye E) from moving by the subject gazing a fixation lamp. The XY direction position detecting system is configured to detect a position in an XY direction (vertical and horizontal displacement with respect to the apparatus body) of a corneal apex of the subject's eye E. The Z-direction position detecting system is configured to detect a position of a front-rear direction (Z-direction) of the corneal apex of the subject's eye E.

The fixation light optical system includes a fixation lamp 32, a cold mirror 33, a relay lens 34, a half mirror 35, the cold mirror 28, the hot mirror 22, the objective lens 23, etc. Light (green light, for example) output from the fixation lamp 32 sequentially passes through the cold mirror 33, the relay lens 34, the half mirror 35, the cold mirror 28, the hot mirror 22, and the lens 23, and is output to the subject's eye E from the inspection window.

The XY direction position detecting system includes an XY position detection light source 36, the cold mirror 33, the relay lens 34, the half mirror 35, the cold mirror 28, the hot mirror 22, the objective lens 23, an imaging lens 37, a position sensor 38, etc.

From the XY position detection light source 36, alignment light for position detection is output. The alignment light is emitted to the anterior segment Ec (cornea) of the subject's eye E from the inspection window through the cold mirror 33, the relay lens 34, the half mirror 35, the cold mirror 28, the hot mirror 22 and the objective lens 23.

At this time, since a corneal surface of the subject's eye E forms a spherical shape, the alignment light is reflected on the corneal surface so as to form a bright spot image inside the corneal apex of the subject's eye E, and the reflected light enters the apparatus body from the inspection window.

Figure 3A:
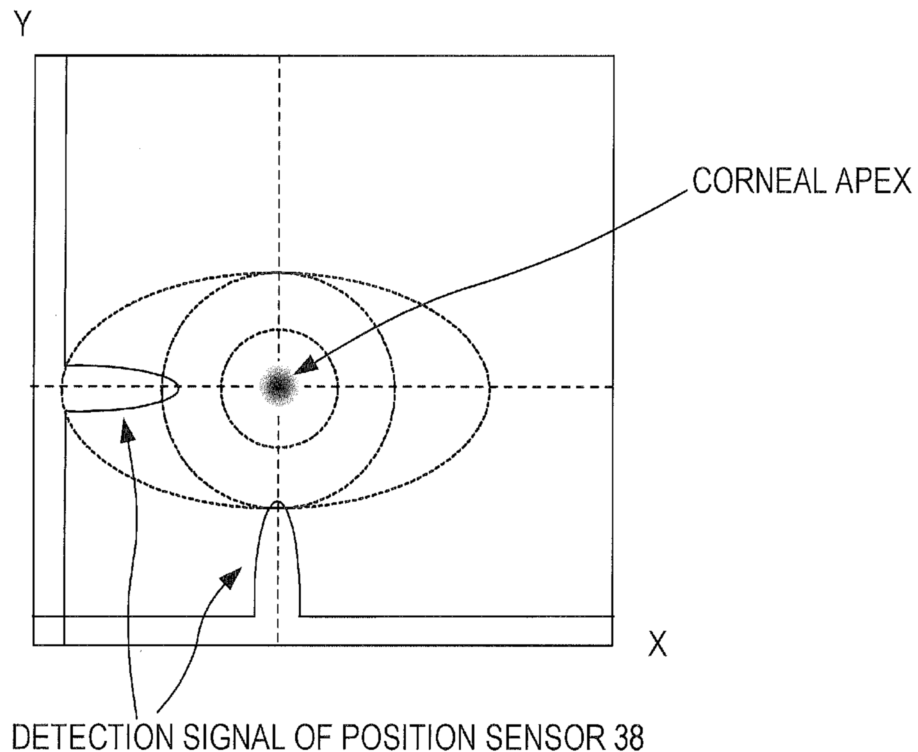
FIG. 3A-3B are views that supplement a description of an alignment process executed by a control unit.

The reflected light (bright spot) from the corneal apex is input to the position sensor 38 through the objective lens 23, the hot mirror 22, the cold mirror 28, the half mirror 35, and the imaging lens 37. A position of the bright spot is detected by the position sensor 38, and thereby a position of the corneal apex (position in the X and Y directions) is detected (see FIG. 3A). The above bright spot is imaged also in a captured image (display image on the monitor 7) of the CCD camera 30.

A detection signal of the position sensor 38 is input to the control unit 3 (computing unit 26) via the optical controller 31. In the computing unit 26 of the control unit 3, a program for implementing some function of the anterior segment three-dimensional image processing apparatus is loaded to the memory or the storage unit 10 in the present embodiment. In the computing unit 26, a CPU executes an alignment process in accordance with this program.

In the alignment process, displacement amounts ΔX, ΔY in the X and Y directions of the detected corneal apex (bright spot), with respect to a predetermined (normal) image acquiring position of the corneal apex, are obtained based on the detection signal (detection result) of the position sensor 38.

The Z-direction position detecting system includes a Z-direction position detecting light source 39, an imaging lens 40, and a line sensor 41. The Z-direction position detecting light source 39 radiates light for detection (slit light or spot light) to the subject's eye E in an oblique direction.

Figure 3B:
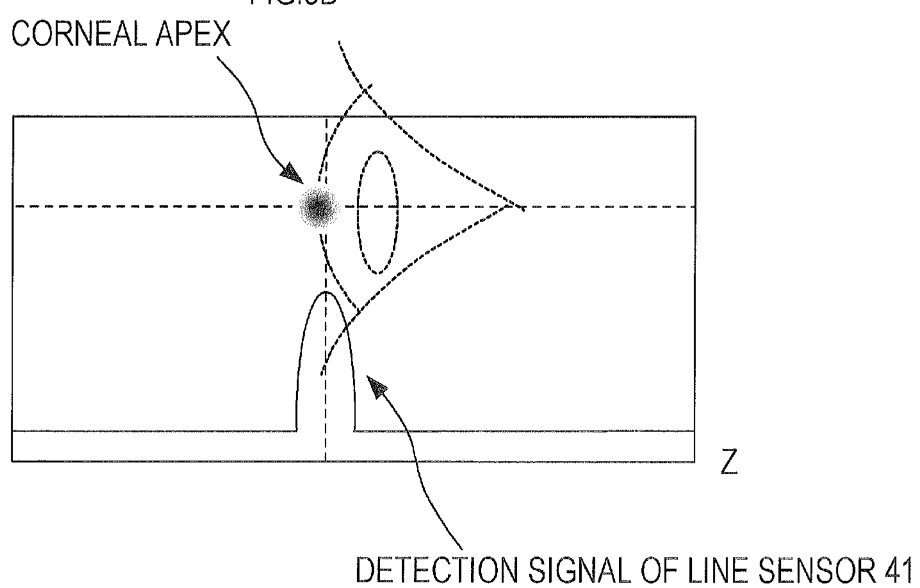

Reflected light in the oblique direction from the cornea enters the line sensor 41 through the imaging lens 40. At this time, depending on the position of the front-rear direction (Z-direction) of the subject's eye E relative to the apparatus body, an entering position of the reflected light that enters the line sensor 41 is different. Therefore, the position (distance) in the Z-direction relative to the apparatus body of the subject's eye E can be detected (see FIG. 3B).

A detection signal of the line sensor 41 is input to the control unit 3 (computing unit 26) via the optical controller 31. At this time, a suitable Z-direction position (distance) relative to the apparatus body of the corneal apex of the subject's eye E is set in advance, and the computing unit 26 of the control unit 3 obtains, in the alignment process, a displacement amount ΔZ in the Z-direction with respect to the position of the corneal apex as an appropriate position of the subject's eye E, based on the detection signal (detection result) of the line sensor 41.

In the alignment process, the computing unit 26 of the control unit 3 stores, in the storage unit 10, the displacement amounts ΔX, ΔY in the X and Y directions of the corneal apex detected by the XY direction position detecting system and the displacement amount ΔZ in the Z-direction of the subject's eye E detected by the Z-direction position detecting system, as alignment information. In this case, the alignment information is stored in a storage format in which format the image data of the two-dimensional tomographic image, corresponding to the alignment information, can be identified.

The computing unit 26 of the control unit 3 controls the galvanometer scanner 20 and performs one-dimensional scanning of the measurement light with respect to the subject's eye E to obtain a two-dimensional tomographic image of one slice plane (B-scan), and furthermore stores, in the storage unit 10, an anterior segment three-dimensional image obtained by repeatedly acquiring a two-dimensional tomographic image (C-scan) by shifting a scanning position of the measurement light with respect to the subject's eye E (in other words, while changing the slice plane). Furthermore, the alignment information described above with respect to each of the two-dimensional tomographic image constituting the anterior segment three-dimensional image is stored in the storage unit 10.

Figure 4A:
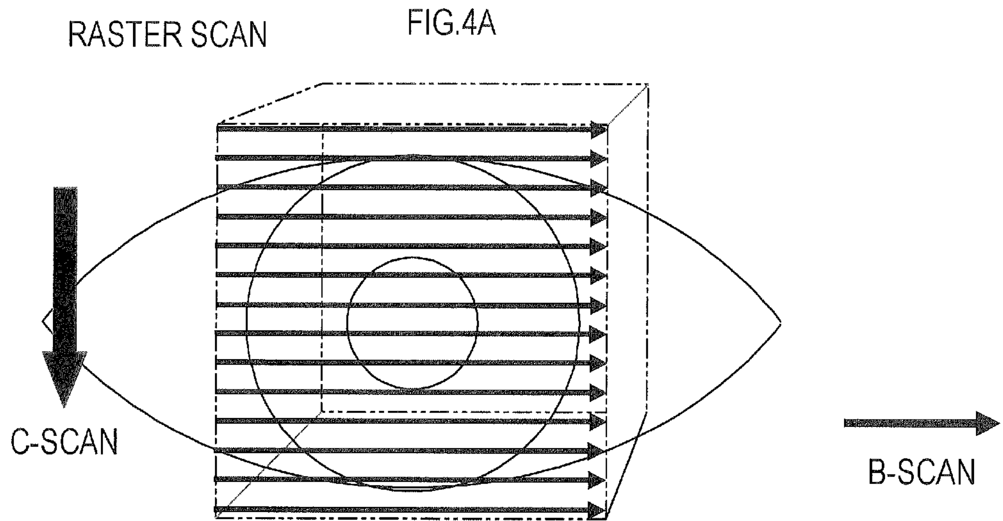
FIGS. 4A-4B are diagrams for explaining a raster scan method.
Figure 4B:
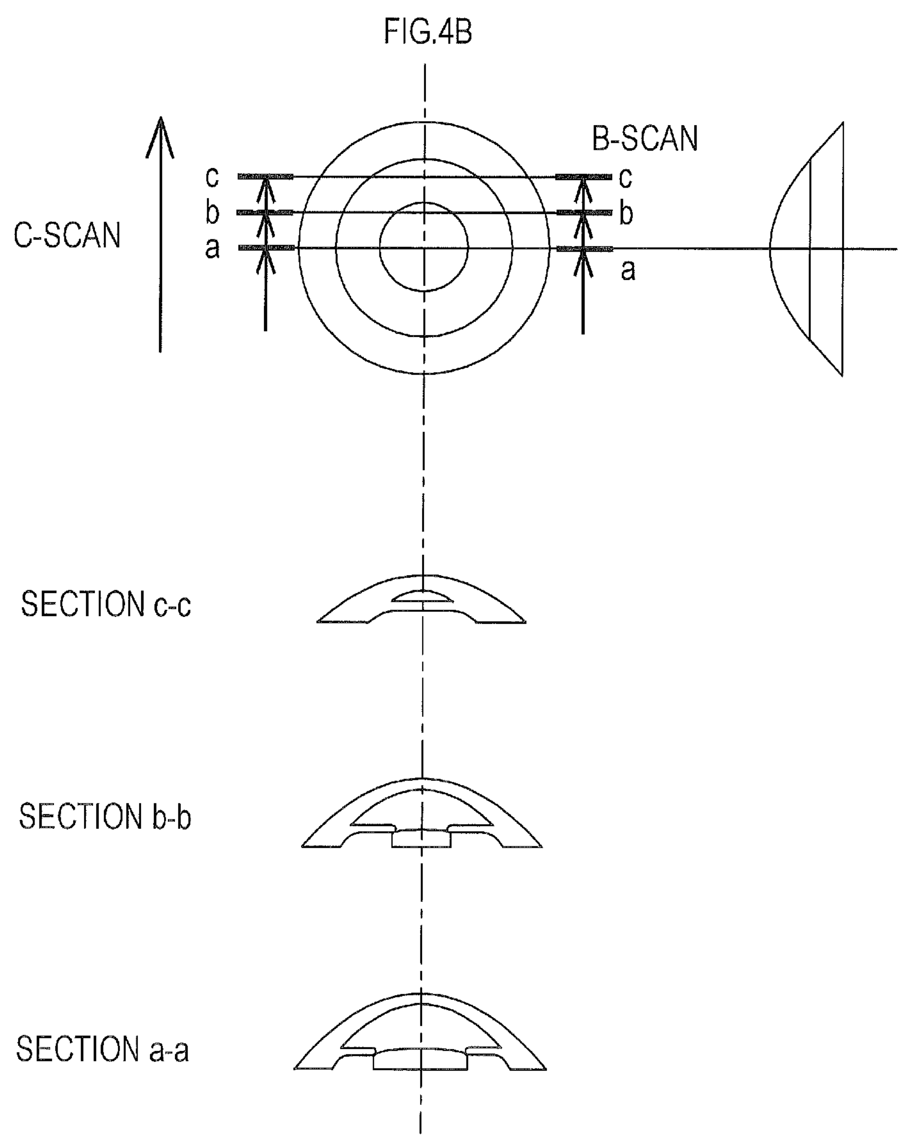
Figure 5A:
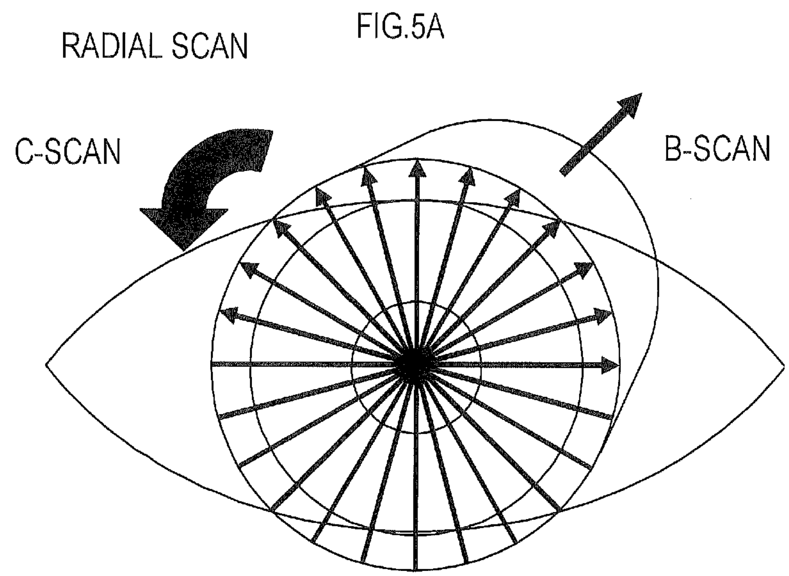
FIGS. 5A-5B are diagrams for explaining a radial scan method.
Figure 5B:
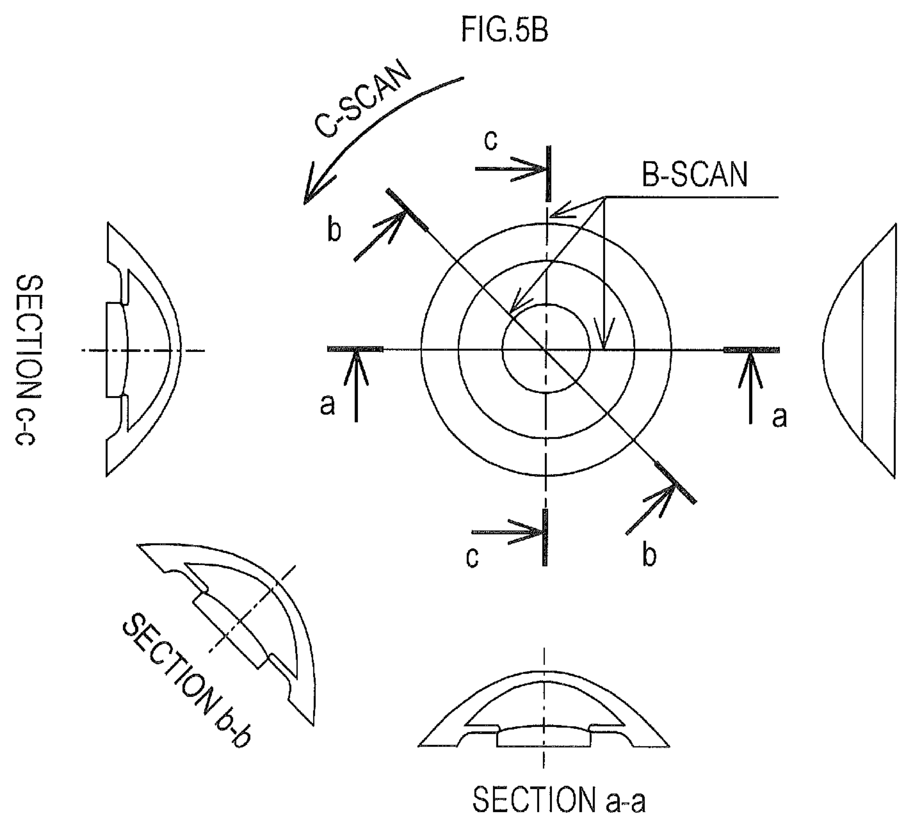

As a scanning method, as described above, there are methods called a raster scan shown in FIGS. 4A-4B and a radial scan shown in FIGS. 5A-5B. According to a result of selection of a measurement target by an operator through the operating unit 8, an appropriate method is selected.

In the present embodiment, when angle analysis is selected as the measurement target, the computing unit 26 of the control unit 3 employs the radial scan as a scan pattern. In particular, the computing unit 26 captures the two-dimensional tomographic image of each slice plane, while setting a radial direction centered on the corneal apex of the subject's eye E as a B-scanning direction and a surface circumferential direction of the anterior segment Ec of the subject's eye E as a C-scanning direction. Hereinafter, it is assumed that the two-dimensional tomographic image of each slice plane, thus captured and stored in the storage unit 10, includes two angles of the anterior segment Ec.

<Anterior Segment Three-dimensional Image Process (First Embodiment)>

Figure 6:
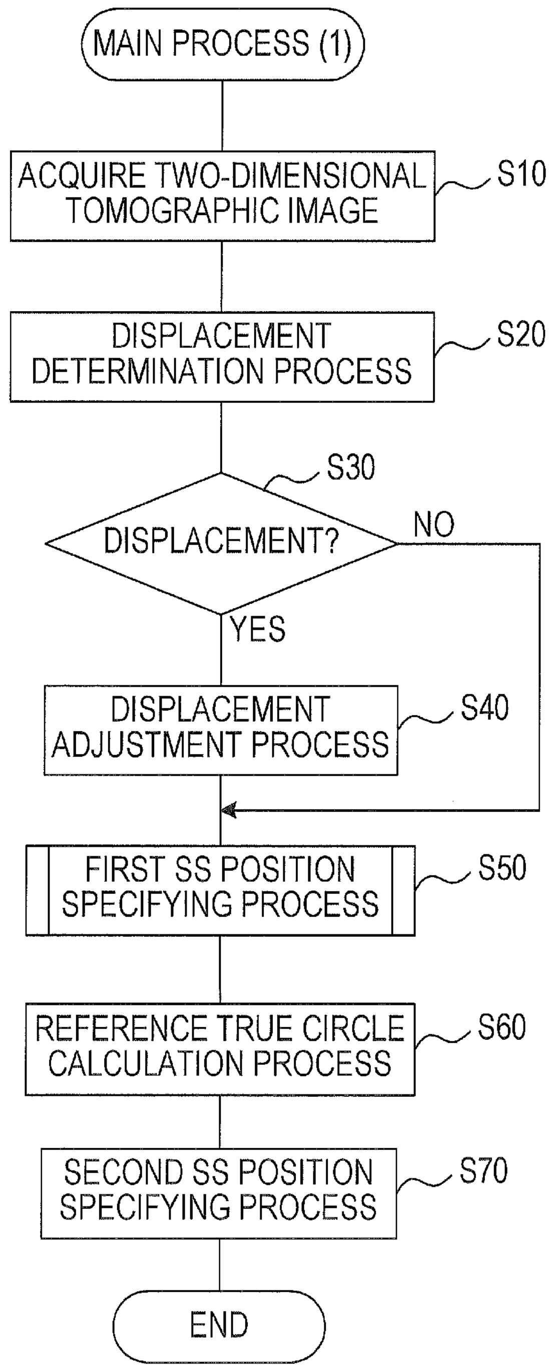
FIG. 6 is a flowchart for explaining an anterior segment three-dimensional image process (main process) executed by an image processing unit in a first embodiment.

The image processing unit 100 includes a microcomputer incorporating a CPU, a memory, etc. A program for implementing the main function of the anterior segment three-dimensional image processing apparatus is stored in the memory or in the storage unit 10. The CPU executes a main process in the anterior segment three-dimensional image process shown in FIG. 6 according to the program.

In the main process, in S10, the image processing unit 100 acquires from the storage unit 10 a two-dimensional tomographic image of each slice plane that constitutes the anterior segment three-dimensional image. Each slice plane is pre-set to form a predetermined angle with respect to an adjacent slice plane on the basis of an optical axis of the measurement light and a C-scan direction of a radial scan.

The setting angle of the present embodiment is 11.25 degrees. That is, the number of a B-scanning direction is thirty-two, and sixteen images of the two-dimensional tomographic images are to be acquired.

Next, in S20, the image processing unit 100 performs a displacement determination process. The displacement determination process is a process of determining whether or not there is a displacement of a spatial coordinate position on the two-dimensional tomographic image of each of the sixteen slice planes acquired in S10.

In this displacement determination process, a determination is made according to presence or absence of a displacement (or, whether or not the displacement is large) of a later described corneal anterior surface curve between each of the two-dimensional tomographic images, in addition to a determination using the alignment information stored in the storage unit 10.

For example, for the two-dimensional tomographic image of each slice plane, based on the alignment information stored in the storage unit 10, if at least one of the displacement amounts ΔX, ΔY, and ΔZ is greater than an allowable predetermined threshold, it is determined that a displacement of the spatial coordinate position exists, and if all the displacement amounts ΔX, ΔY, and ΔZ are equal to or less than the allowable threshold, a threshold determination on the displacement of the corneal anterior surface curve is performed.

Then, when it is determined that there is a displacement of the corneal anterior surface curve, it is determined that the displacement of the spatial coordinate position exists, and if it is determined that there is no displacement of the corneal anterior surface curve, it is determined that no displacement of the spatial coordinate position exists.

As such, in the present embodiment, two techniques are used, i.e., a technique of determination using the alignment information and a technique of determination in accordance with the displacement of the corneal anterior surface curve. In one embodiment, only one of the techniques can instead be used.

Next, in S30, the image processing unit 100 branches the process according to the determination result in S20. In S20, if it is determined that the displacement of the spatial coordinate position exists, the process moves to S40, and if it is determined the displacement of the spatial coordinate position does not exist, the process proceeds to S50.

In S40, a displacement adjustment process is executed. The displacement adjustment process is process for adjusting the displacement of the space coordinate position of the two-dimensional tomographic image that was determined to have the displacement of the spatial coordinate position in S20. In the displacement adjustment process of the present embodiment, an offset amount ΔX' is obtained so that the displacement amounts ΔX, ΔY, and ΔZ based on the alignment information above satisfy, for example, a relational expression (1) below.

Figure 7A:
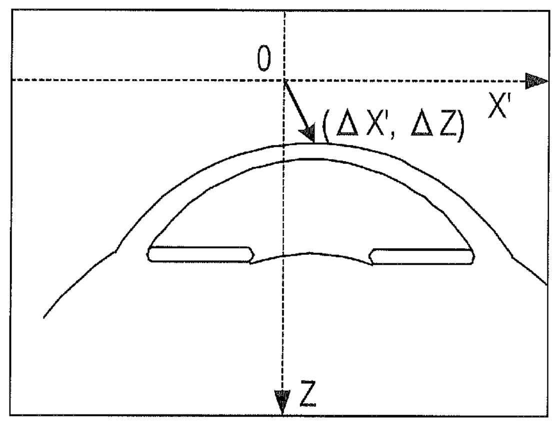
FIGS. 7A-7B are views that supplement a description of a displacement adjustment process in the first embodiment.
Figure 7B:
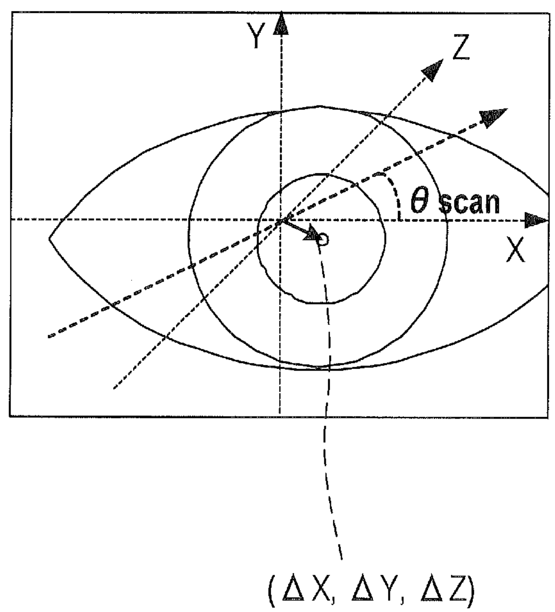

Here, offset amounts of the spatial coordinate position in the two-dimensional tomographic image are assumed as ΔX', ΔZ. The offset amount ΔX' is a correction amount of the spatial coordinate position in an X'-direction, when the X'-direction is a direction perpendicular to the Z-direction on the two-dimensional tomographic image as shown in FIG. 7A. Also, θscan refers to an angle formed by the B-scanning direction of the radial scan with respect to the X-direction, as shown in FIG. 7B.

[Expression 1]

$$\Delta X' = (\Delta X^2 + \Delta Y^2)^{-1/2} \times \cos(\tan^{-1}(\Delta Y/\Delta X) - \theta\ \text{scan}) \quad (1)$$

The above relational expression (1) may be used as approximation formula in the case that the offset amount ΔX' is small (for example, 300 μm or less). Also, in the displacement adjustment process, in addition to the adjustment (correction) using the alignment information stored in the storage unit 10 as described above, a later described displacement of the corneal anterior surface curve may be corrected between each of the two-dimensional tomographic images (see second embodiment).

In S40, as above, the displacement adjustment process is performed to all the two-dimensional tomographic images stored in the storage unit 10. Thereby, the spatial coordinate position of each image is combined to reconstruct the anterior segment three-dimensional image.

In the present embodiment, as described above, two techniques, that is, a technique of correction using the alignment information and a technique of correcting a displacement of the corneal anterior surface curve, are used, but instead only one of the techniques can be used.

By using the two techniques, however, it is possible to complement errors having different properties from each other. For example, in the technique of correction using the alignment information, there is a possibility that an error occurs due to a failure to consider a rotation movement of the subject's eye E (eyeball).

In the technique of correcting a displacement of the corneal anterior surface curve, there is a possibility that an error occurs when the eyeball had a large movement. By using the both techniques, it is possible to complement errors having different properties.

Next, in S50, the image processing unit 100 performs a process for selecting four two-dimensional tomographic images as representative images, from among the sixteen two-dimensional tomographic images of the respective slice planes obtained in S10, and identifying two SS positions indicating the spatial coordinate position of a scleral spur of the anterior segment Ec for each representative image (hereinafter "first SS position specifying process").

In the present embodiment, eight SS positions are identified from the four representative images. In this embodiment, four two-dimensional tomographic images in which an angle formed by the mutual slice planes is a predetermined angle (e.g., 30 degrees) or more are selected as the four representative images.

Figure 9A:
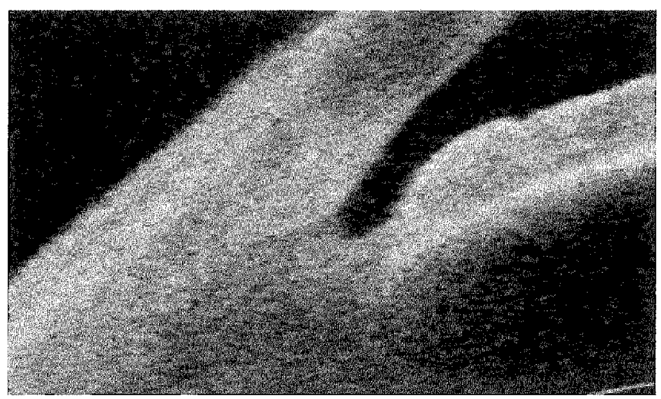
FIGS. 9A-9D are views that supplement a description of the first SS position specifying process.

FIG. 8 shows processing details of S50. In the first SS position specifying process as shown in FIG. 8, the image processing unit 100 extracts an image locally including a vicinity of angles of the anterior segment Ec (hereinafter referred to as " local image": see FIG. 9A) from the representative image, in S110.

Next, in S120, the image processing unit 100 calculates brightness gradient for each pixel of the image data of the local image extracted in S110 by, for example, obtaining a difference of brightness between adjacent pixels in the Z direction.

Then, based on the brightness gradient in the local image above, in S130, the image processing unit 100 detects an edge line showing a corneal posterior surface (hereinafter referred to as "corneal posterior surface edge line") of the anterior segment Ec, and, in S140, detects an edge line showing an iris anterior surface in the anterior segment Ec (hereinafter referred to as "iris anterior surface edge line").

In the image data of the local image above, the brightness gradient of the pixels on the corneal posterior surface edge line and the iris anterior surface edge line is the highest. Thus, for example, by appropriately setting a threshold value of the brightness gradient, it is possible to extract (detect) the corneal posterior surface edge line and the iris anterior surface edge line from the local image.

Figure 9B:
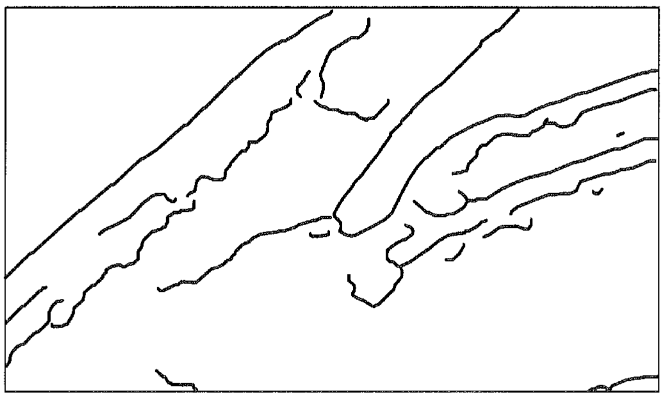

Next, in S150, the image processing unit 100, by variably setting the threshold value in the image data of the local image, generates image data including edge lines (hereinafter referred to as "edge image": see FIG. 9B) that can possibly define each site in the anterior segment Ec, in addition to the corneal posterior surface edge line and the iris anterior surface edge line.

In S155, the image processing unit 100 extracts, from the edge image, a predetermined region that is estimated to include the SS position on the corneal posterior surface edge line detected in S130.

For example, in S155, when the iris anterior surface edge line could have been detected in S140, the image processing unit 100 limits the predetermined region from the edge image, based on an inflection point of an edge line (corresponding to an angle recess of the anterior segment Ec) formed by connecting the two edge lines, i.e., the corneal posterior surface edge line and the iris anterior surface edge line.

Figure 9C:
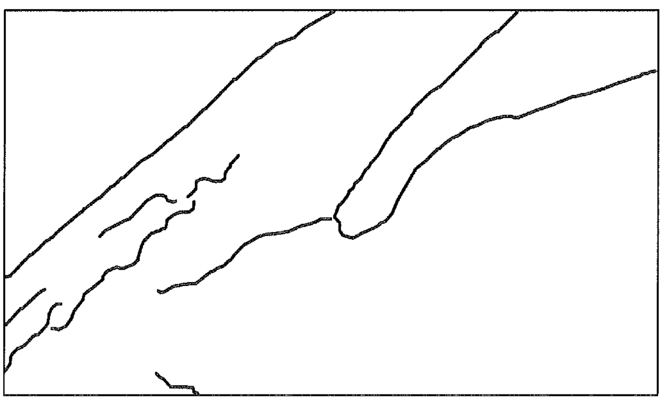
Figure 9D:
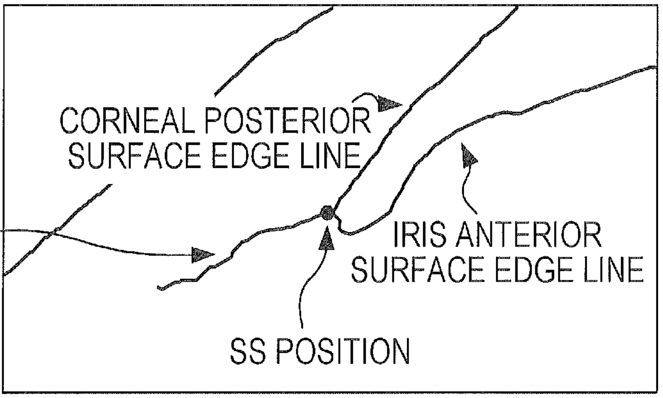

Then, in S160, the image processing unit 100 removes from the edge image the edge lines outside the predetermined region extracted in S150, as unnecessary edge lines. For example, unnecessary edge lines that are branched from the corneal posterior surface edge line outside the predetermined region and unnecessary edge lines that branch from the iris anterior surface edge line outside the predetermined region are removed (see FIG. 9C).

In S170, by the removal of unnecessary edge lines in S160, the image processing unit 100 extracts a candidate edge line that is a candidate of an edge line showing a boundary between the sclera and uvea (hereinafter, "sclera-uveal edge line") in the anterior segment Ec.

Next, in S180, for each candidate edge line extracted in S170, the image processing unit 100 calculates a magnitude (intensity of the edge) of the brightness gradient in a transverse direction, and identifies, from among each candidate edge line, the edge line that has a maximum brightness gradient as a sclera-uveal edge line.

Then, in S190, the image processing unit 100 determines whether or not the iris anterior surface edge line could have been detected in S140, and branches the process in accordance with a determination result. That is, depending on the subject's eye E, there is a case in which the angle is closed. In such a case, the iris anterior surface edge line is projected as if it were integrated with the corneal posterior surface edge line. The iris anterior surface edge line may not be detected.

Here, if it is determined that the image processing unit 100 could have detected the iris anterior surface edge line, the process proceeds to S200. If it is determined that the image processing unit 100 has failed to detect the iris anterior surface edge line, the process proceeds to S210.

In S200, the image processing unit 100 identifies a spatial coordinate position indicating an intersection of the sclera-uveal edge line identified in S180, the corneal posterior surface edge line detected in S130 and the iris anterior surface edge line detected in S140, as the SS position. Then, the process proceeds to S220.

On the other hand, in S210, the image processing unit 100 identifies a spatial coordinate position indicating an intersection of the sclera-uveal edge line identified in S180 and the corneal posterior surface edge line detected in S130, as the SS position. For example, as a method of identifying the intersection (that is, the SS position) of the sclera-uveal edge line and the corneal posterior surface edge line, several methods can be employed.

In one example, it is possible to identify the SS position, on the basis of the shape of an edge line (referred to as "target edge line" below) formed by connecting the edge lines of both the sclera-uveal edge line and the corneal posterior surface edge line. In the edge image, taking advantage of the fact that a slope of the sclera-uveal edge line and a slope of the corneal posterior surface edge line are different, for example, a point where the slope of the above-mentioned target edge line greatly varies in a curved manner (inflection point) can be identified as the SS position.

Further, for example, it is also possible to specify the SS position, on the basis of the information of the brightness gradient on the target edge line. That is, in the edge image, taking advantage of the fact that the brightness gradient on the corneal posterior surface edge line is higher than the brightness gradient on the sclera-uveal edge line, for example, a point where the brightness gradient greatly varies in the above-mentioned target edge line can be identified as the SS position.

In S220, the image processing unit 100 determines whether or not a predetermined number of SS positions (two SS positions in this embodiment) could have been identified from each of all the representative images (four representative images in this embodiment). If all the SS positions (eight SS positions in the embodiment) could have been identified, the process returns to the main process (S60). If there is any unspecified SS position in the representative images, the process returns to S110 and continues the first SS position specifying process.

Returning to the main process (S60), the image processing unit 100 calculates a function representing a reference true circle (see FIG. 10) passing through the at least three SS positions of the plurality of (eight in this embodiment) SS positions identified in S50 on spatial coordinates. Specifically, in the present embodiment, a reference true circle on a space plane is obtained which passes through the at least three SS positions from among the eight SS positions, and a distance of which from the remaining SS positions is minimum (in other words, the remaining SS positions are arranged to be most approximate on the function above).

As such, by obtaining the reference true circle such that the remaining SS positions from among the eight SS positions are approximately positioned, it becomes possible to properly disperse errors between images, and it is possible to improve accuracy in automatic identification of the SS positions. As the reference true circle, a true circle is generally employed. Other than a complete true circle, a circle close to a true circle may be employed.

In S70, the image processing unit 100 performs a process that identifies the remaining SS positions (hereinafter also referred to as "second SS position specifying process") based on the function of the reference true circle calculated in S60, for the plurality of (twelve in this embodiment) images (hereinafter "non-representative images") other than the plurality of (four in this embodiment) representative images, from among the plurality of (sixteen in this embodiment) two-dimensional tomographic images which constitute the anterior segment three-dimensional image.

Specifically, the image processing unit 100 identifies each point corresponding to the B-scan direction in each of the non-representative images on the reference true circle obtained in S60, as the SS position in the corresponding non-representative image. Then, the image processing unit 100 ends the main process.

Figure 11:
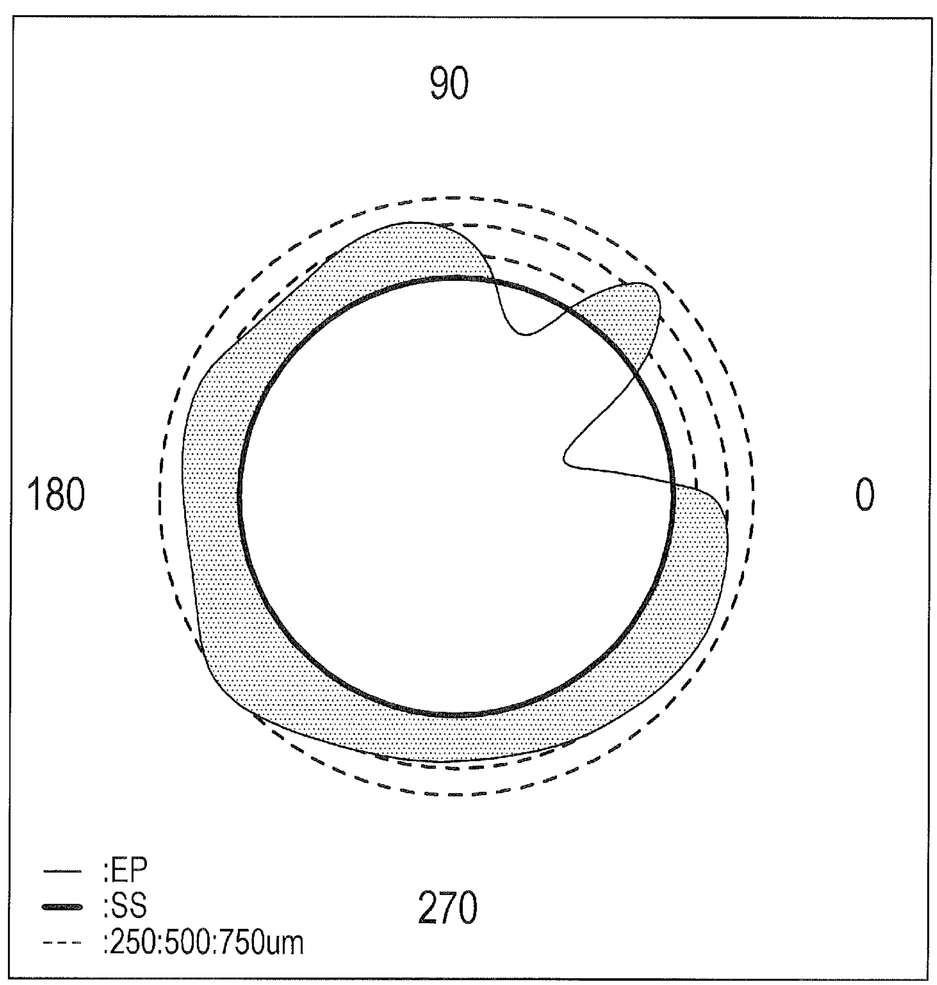
FIG. 11 is a chart illustrating one aspect of an angle analysis (analysis image showing an ITC)

The image processing unit 100, by using the SS positions obtained in all the slice planes as such, can, for example, generate analysis images (see FIG. 11) that show an angle portion EP which is closed beyond the SS position (portion where the corneal posterior surface is in contact with the iris anterior surface) in a chart as an iridotrabecular contact (ITC) portion. Then, these images are output to the monitor 7 in response to operation instructions by the operator through the operating unit 8.

<Second Embodiment>

Now, the second embodiment of the present invention will be described. Since the second embodiment differs from the first embodiment only in some parts of the main process (anterior segment three-dimensional image process) executed by the image processing unit 100, explanation for the others will not be repeated.

Specifically, in the anterior segment three-dimensional image process of the first embodiment, by performing displacement adjustment process (S40), each of the spatial coordinate positions of the two-dimensional tomographic images is adjusted. The anterior segment three-dimensional image is reconstructed, and the SS position for each of the two-dimensional tomographic images constituting the reconstructed anterior segment three-dimensional image is identified (S50~S70).

In contrast, the anterior segment three-dimensional image process of the second embodiment differs in that a determination of SS position is made using the parameters that are calculated for adjusting the displacement of the spatial coordinate position of each of the two-dimensional tomographic images, without performing reconstruction of the anterior segment three-dimensional image. According to the anterior segment three-dimensional image process in the second embodiment, since reconstruction of the anterior segment three-dimensional image is not necessary, it is possible to improve the whole processing speed including the angle analysis.

<Anterior Segment Three-dimensional Image Process (Second Embodiment)>

Figure 12:
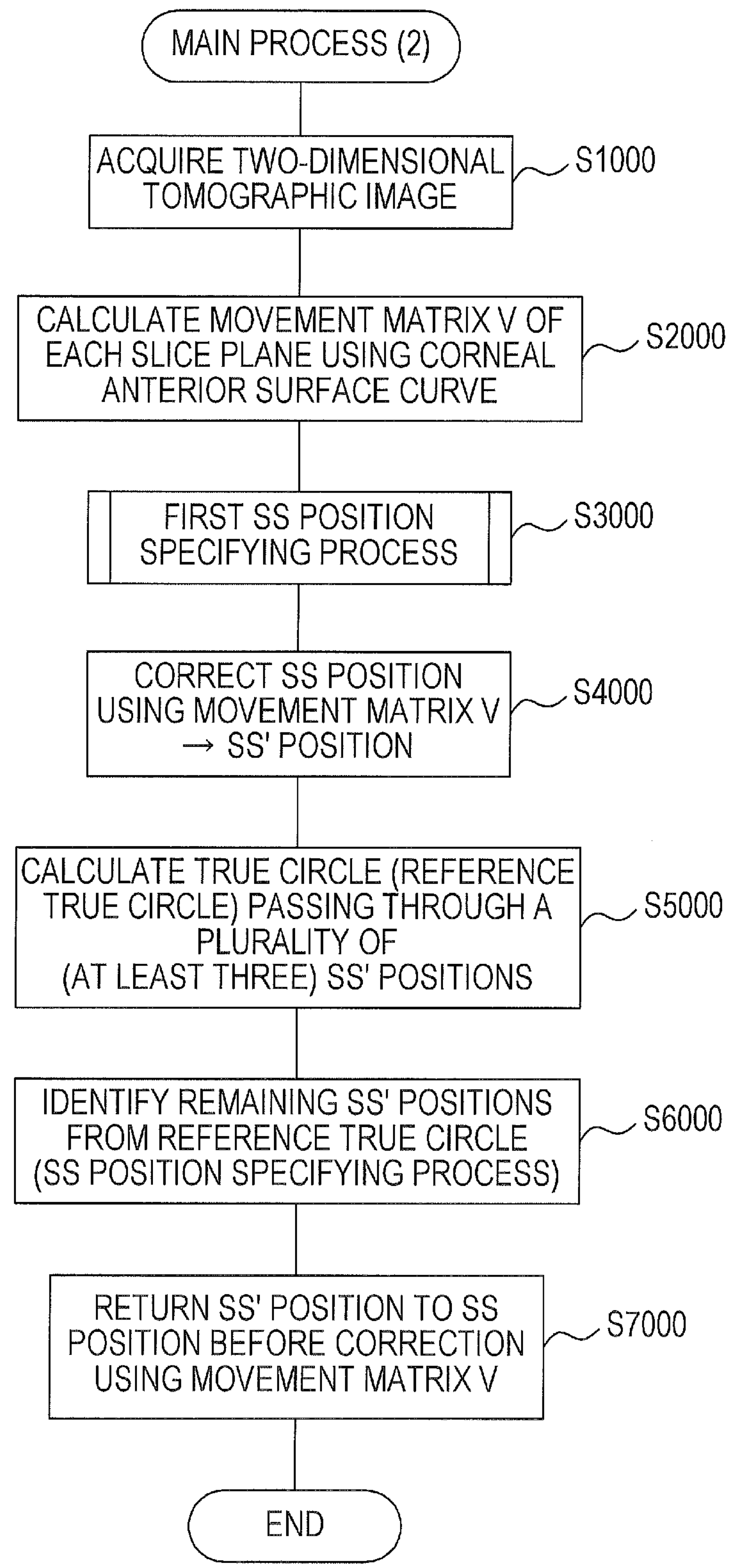
FIG. 12 is a flowchart illustrating the anterior segment three-dimensional image process (main process) by the image processing unit executed in a second embodiment.

In the main process of the second embodiment shown in FIG. 12, the image processing unit 100 acquires the two-dimensional tomographic image of each slice plane that constitutes the anterior segment three-dimensional image from the storage unit 10, in S1000, as in the first embodiment.

In the second embodiment, each slice plane is pre-set to form a predetermined angle with respect to the adjacent slice plane in the C-scan direction of the radial scan, on the basis of the optical axis of the measurement light. The setting angle of this embodiment is 5.625 degrees. That is, the number of the B-scanning direction is sixty-four, and thirty-two two-dimensional tomographic images are to be acquired.

Then, in S2000, the image processing unit 100 calculates a movement matrix V for mutually adjusting the spatial coordinate positions on the basis of the position of the corneal anterior surface, between the two-dimensional tomographic image of each of the thirty-two slice planes acquired in S1000 and the two-dimensional tomographic image of the adjacent other slice plane, one by one.

Specifically, the image processing unit 100 first extracts a curve representing a shape of the corneal anterior surface (hereinafter, "corneal anterior surface curve"), using a well known technique such as, for example, pattern matching, from each one of the two-dimensional tomographic images and an adjacent one of the two-dimensional tomographic images.

Figure 13:
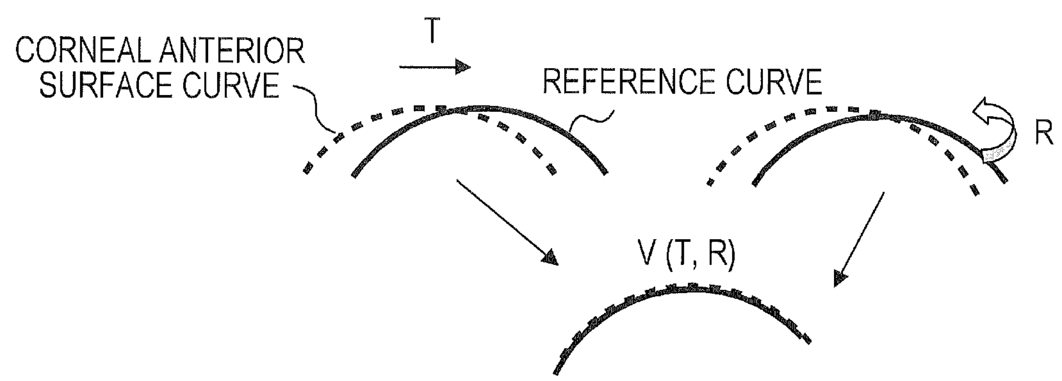
FIG. 13 is a view that supplements a description of a displacement adjustment process in the second embodiment.

Then, for example, as shown in FIG. 13, for each of the extracted corneal anterior surface curves, the image processing unit 100 translates and rotates one to the other side, obtains a reference corneal anterior surface curve (referred to as "reference curve" below) that minimizes a translation distance T and a rotation angle R, and calculates an input expression of the corneal anterior surface curve of each of the two-dimensional tomographic images having this reference curve as an output value, as the corresponding movement matrix V.

For example, this calculation of the movement matrix V is performed for all of the two-dimensional tomographic images, and an average reference curve is obtained for all of the two-dimensional tomographic images. On the basis of the average reference curve, the movement matrix V for each of the two-dimensional tomographic images is corrected. The movement matrix V thus calculated is temporarily stored in the memory in association with the two-dimensional tomographic image of each corresponding slice plane.

This S2000 determines whether or not a displacement of the corneal anterior surface curve exists between each of the two-dimensional tomographic images (or whether or not the displacement is large), for all of the two-dimensional tomographic images, and is performed for cases in which a displacement of the corneal anterior surface curve exists.

Next, in S3000, the image processing unit 100 selects three two-dimensional tomographic images from among the two-dimensional tomographic images of the thirty-two slice planes acquired in S1000 and of which the movement matrix V has been calculated at S2000, as representative images. Then, the image processing unit 100 performs a process (first SS position specifying process) that identifies two SS positions indicating the spatial coordinate position of the scleral spur of the anterior segment Ec in each of the representative images.

In the second embodiment, six SS positions are identified from the three representative images. In the second embodiment, three two-dimensional tomographic images in which an angle formed by the mutual slice planes is a predetermined angle (45 degrees, for example) or more are selected as the three representative images. Particulars of the first SS position specifying process are the same as those of the first embodiment, and thus are not repeated.

In S4000, the image processing unit 100 adjusts (corrects) each of the spatial coordinate positions, using the movement matrix V calculated in S2000, for the plurality of (six in this embodiment) SS positions identified in S3000 (first SS position specifying process).

Figure 10:
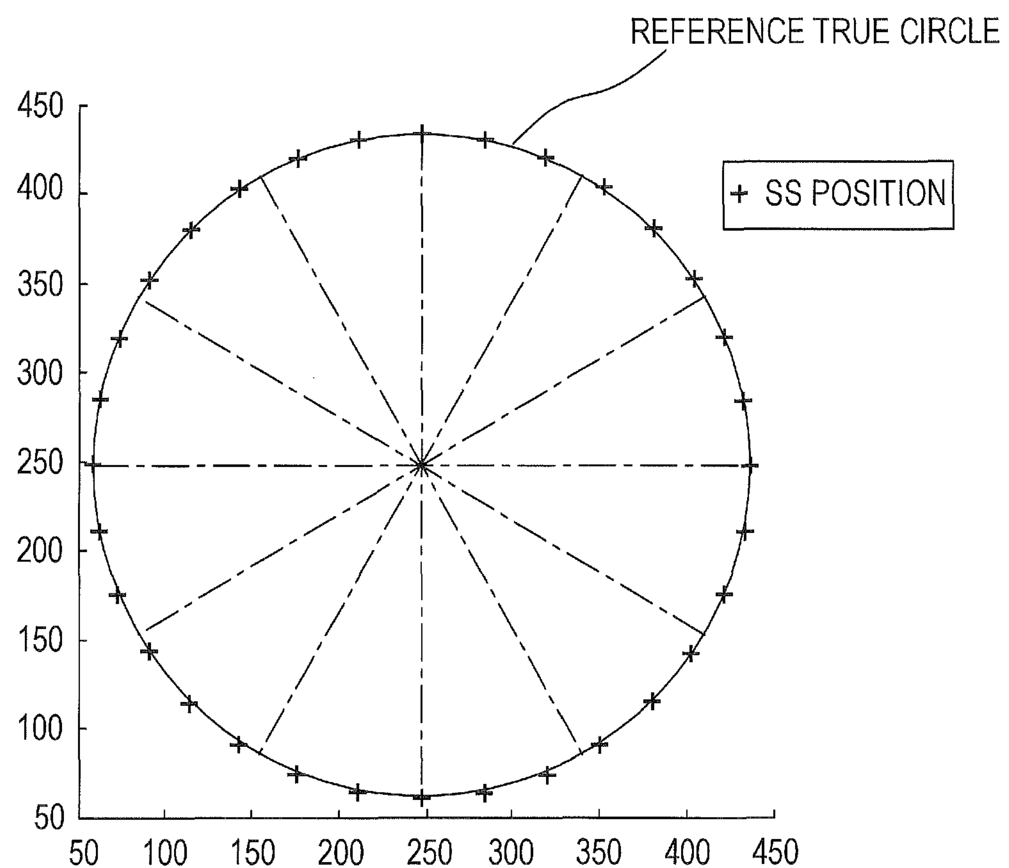
FIG. 10 is a view that supplements a calculation of a reference true circle executed in the main process and a description of a second SS position specifying process.

In S5000, from among the plurality of (six in this embodiment) SS positions (referred to as “SS' positions” hereinafter) corrected in S4000, the image processing unit 100 calculates a function representing a reference true circle passing through at least three SS' positions on spatial coordinates (see FIG. 10).

Specifically, in the second embodiment, a reference true circle on a spatial plane is obtained that has a diameter equal to a distance between the two SS' positions identified by one representative image and that passes through at least the remaining one SS' position. In this case, only by identifying at least one SS' position, in addition to the two SS' positions constituting the diameter, the reference true circle on the space plane is determined.

Therefore, it is possible to reduce the number of two-dimensional tomographic images (representative images) used to determine the reference true circle. This makes it possible to improve a process that can be automated.

In S6000, the image processing unit 100 performs a process (second SS position specifying process) that identifies the remaining SS' positions for the plurality of (twenty-nine in this embodiment) images (“non-representative images” hereinafter) other than the plurality of (three in this embodiment) representative images, from among the plurality of (thirty-two in this embodiment) two-dimensional tomographic images that constitute the anterior segment three-dimensional image, based on the function of the reference true circle calculated in S5000. Specifically, on the true circle obtained in S5000, each point corresponding to the B-scan direction in each of the non-representative images is identified as the SS' position in the corresponding non-representative image.

Then, in S7000, the image processing unit 100 returns the SS' positions in all of the two-dimensional tomographic images thus identified to the SS positions before correction, using the movement matrix V calculated in S2000, thereby to calculate (identify) the SS positions in all the two-dimensional tomographic images. Then, the image processing unit 100 ends the main process.

<Major Effect>

As described above, in the anterior segment OCT1, in the main process, identification of three or more SS positions is automatically accepted (S50, for example), using two or more representative images, from among the two-dimensional tomographic images for which whether or not there is a displacement of the spatial coordinate position (S10~S20, for example) have been determined, and the function showing the reference true circle passing through the at least three SS positions on spatial coordinates is calculated (S60, for example). Then, the SS positions, etc. (remaining SS positions) in the two-dimensional tomographic images (non-representative images) other than the representative images are identified based on the function of the reference true circle (S70, for example).

Therefore, according to the anterior segment OCT1, since it is not necessary at all for the operator to input the SS positions by pointing, it is possible to significantly reduce the time to start creating a chart indicating, for example, an ITC. Therefore, the anterior segment OCT1 can be effectively utilized clinically, by automating the entire process, in angle analysis by means of an anterior segment OCT.

Also, in the anterior segment OCT1, in the first SS position specifying process, on the basis of the information of the brightness gradient in the representative image, the sclera-uveal edge line showing the boundary between the sclera and the uvea in the anterior segment Ec and the corneal posterior surface edge line showing the corneal posterior surface of the anterior segment Ec are detected (identified), and the intersection of the identified sclera-uveal edge line and corneal posterior surface edge line is identified as the SS position.

Furthermore, if the iris anterior surface edge line showing the iris anterior surface of the anterior segment Ec could have been detected (identified) on the basis of the information of the brightness gradient in the representative image, the intersection of the identified sclera-uveal edge line, corneal posterior surface edge line and iris anterior edge line is identified as the SS position.

Thus, for example, in a two-dimensional tomographic image where the iridotrabecular contact part (ITC) is not present, the above intersection becomes easier to extract by using the three edge lines. Therefore, accuracy in automatic identification of the SS position can be improved.

<Other Embodiments>

The first and second embodiments of the present invention have been described above. However, the present invention is not limited to these embodiments, and can be implemented in various aspects without departing from the scope of the present invention.

For example, in the first embodiment, in the anterior segment three-dimensional image process (main process), the SS position is automatically identified by performing the first SS position specifying process (S50). Instead of this, here, it is also possible to accept input of the SS position by pointing of the operator through the operating unit 8. Also, in the above first embodiment, in the first SS position specifying process (S50), eight SS positions are automatically identified. However, if at least three SS positions are automatically identified, the reference true circle can be calculated.

That is, according to the anterior segment OCT1, if the operator only enters a total of three SS positions in two of the two-dimensional tomographic images, all the other SS positions in the two-dimensional tomographic images that constitute the anterior segment three-dimensional image are automatically identified. Therefore, according to the anterior segment OCT1, since at least the need by the operator to identify all the SS positions in the two-dimensional tomographic images is eliminated, it is possible to shorten the time to start creating a chart indicating, for example, an ITC. Thus, in angle analysis, the anterior segment OCT1 can be effectively utilized clinically, by increasing the number of processes that can be automated.

In the second embodiment, in the anterior segment three-dimensional image process (main process), after performing correction of the SS positions using the corneal anterior curve (S2000, S4000) to identify all the SS' positions, the process of returning to the SS positions before correction is performed (S7000). However, it is not always necessary to do in this manner. For example, by performing such a correction to all the two-dimensional tomographic images stored in the storage unit 10, it is possible to adjust the spatial coordinate position of each image and reconstruct the anterior segment three-dimensional image.

In the above embodiment, the control unit 3 is configured to store in the storage unit 10 the two-dimensional tomographic image of each slice plane that constitutes the anterior segment three-dimensional image. However, it is also possible to store the images, for example, in a server, etc. on the Internet.

In the above embodiment, in the anterior segment OCT1, the control unit 3 and the image processing unit 100 are configured separately. However, the control unit 3 may perform the process executed by the image processing unit 100. The image processing unit 100 may perform the process executed by the control unit 3.

Furthermore, an apparatus including the image processing unit 100 may be configured separately from the anterior segment OCT1. The apparatus, by being communicatively connected between the anterior segment OCT1 and the server, may perform various processes.

A program for causing this apparatus to execute various processes may be stored in the storage unit 10 or in the above server. The image processing unit 100 may load the program to perform various processes.

<Reference Invention>

As inventions related to the present application, it is possible to include the following inventions.

(1) A two-dimensional tomographic image processing apparatus comprising:

an image acquiring unit that acquires a two-dimensional tomographic image including an angle of an anterior segment of a subject's eye, by means of an optical coherence tomography device;

a candidate extracting unit that extracts a candidate edge line that is a candidate for a sclera-uveal edge line showing a boundary between a sclera and a uvea in the anterior segment, from a predetermined region of the two-dimensional tomographic image acquired by the image acquiring unit; and a specifying unit that identifies the sclera-uveal edge line, based on brightness gradient information of the candidate edge line extracted by the candidate extracting unit.

(2) The two-dimensional tomographic image processing apparatus according to (1) above, further comprising:

a corneal posterior surface edge line detecting unit that detects a corneal posterior surface edge line showing a corneal posterior surface of the anterior segment of the subject's eye in the two-dimensional tomographic image;

an iris anterior surface edge line detecting unit that detects an iris anterior surface edge line showing an iris anterior surface of the anterior segment of the subject's eye in the two-dimensional tomographic image; and a region extracting unit that extracts the predetermined region, based on the corneal posterior surface edge line detected by the corneal posterior surface edge line detecting unit and the iris anterior surface edge line detected by the iris anterior surface edge line detecting unit.

(3) The two-dimensional tomographic image processing apparatus according to (1) or (2) above, further comprising:

a corneal posterior surface edge line detecting unit that detects a corneal posterior surface edge line showing a corneal posterior surface of the anterior segment of the subject's eye in the two-dimensional tomographic image; and a SS position specifying unit that identifies an intersection of the sclera-uveal edge line identified by the specifying unit and the corneal posterior surface edge line detected by the corneal posterior surface edge line detecting unit as a SS position indicating the sclera spur of the anterior segment of the subject's eye in the two-dimensional tomographic image.

(4) The two-dimensional tomographic image processing apparatus according to (3) above, wherein the SS position specifying unit identifies an inflection point of an edge line formed by connecting the sclera-uveal edge line identified by the specifying unit and the corneal posterior surface edge line detected by the corneal posterior surface edge line detecting unit, as the SS position.

(5) The two-dimensional tomographic image processing apparatus according to (3) or (4) above, wherein the SS position specifying unit identifies the SS position based on brightness gradient information of an edge line formed by connecting the sclera-uveal edge line identified by the specifying unit and the corneal posterior surface edge line detected by the corneal posterior surface edge line detecting unit.

(6) The two-dimensional tomographic image processing apparatus according to one of (3) to (5) above, further comprising an iris anterior surface edge line detecting unit that detects an iris anterior surface edge line showing an iris anterior surface of the anterior segment in the two-dimensional tomographic image, wherein the SS position specifying unit identifies an intersection of the sclera-uveal edge line identified by the specifying unit, the corneal posterior surface edge line detected by the corneal posterior surface edge line detecting unit, and the iris anterior surface edge line detected by the iris anterior surface edge line detecting unit, as the SS position.

(7) A program for causing a computer to function as the image acquiring unit, the candidate extracting unit and the specifying unit described in (1) above.

(8) A two-dimensional tomographic image processing method comprising:

an image acquiring step in which a two-dimensional tomographic image including an angle of an anterior segment of a subject's eye is acquired by means of an optical coherence tomography device;

a candidate extracting step in which a candidate edge line that is a candidate for a sclera-uveal edge line showing a boundary between a sclera and a uvea in the anterior segment is extracted from a predetermined region of the two-dimensional tomographic image acquired in the image acquiring step; and a specifying step in which the sclera-uveal edge line is identified based on brightness gradient information of the candidate edge line extracted in the candidate extracting step.

According to the two-dimensional tomographic image processing apparatus of (1) above, for example, by displaying the identified sclera-uveal edge line, it is possible to have the operator to input by pointing the intersection of the corneal posterior surface and the iris anterior surface around the angle that are displayed in a relatively easily visible manner in each of the two-dimensional tomographic images and the displayed sclera-uveal edge line as the SS position. Therefore, it is possible to reduce the trouble of input by the operator, or to reduce input errors. Accordingly, it is possible to reduce the burden on the operator.

What is claimed is:

1. An anterior segment three-dimensional image processing apparatus that receives and processes an anterior segment three-dimensional image of a subject's eye by means of an optical coherence tomography device, the apparatus comprising:

a first SS position specifying unit that accepts identification of at least three SS positions indicating a spatial coordinate position of a scleral spur of the subject's eye, using at least two representative images from among a plurality of two-dimensional tomographic images constituting the anterior segment three-dimensional image;

a true circle calculating unit that calculates a reference true circle passing through the at least three SS positions of the SS positions identified by the first SS position specifying unit in the anterior segment three-dimensional image; and a second SS position specifying unit that identifies the SS positions in non-representative images other than the representative images from among the plurality of two-dimensional tomographic images, based on the reference true circle calculated by the true circle calculating unit.

2. The anterior segment three-dimensional image processing apparatus according to claim 1, further comprising:

a determining unit that determines whether or not there is a displacement of the spatial coordinate position on the plurality of two-dimensional tomographic images; and a position adjusting unit that adjusts the displacement of the spatial coordinate position when it is determined that there is a displacement of the spatial coordinate position by the determining unit.

3. The anterior segment three-dimensional image processing apparatus according to claim 2, wherein the position adjusting unit adjusts the displacement of the spatial coordinate position based on a corneal anterior surface shape of the subject's eye in the two-dimensional tomographic images.

4. The anterior segment three-dimensional image processing apparatus according to claim 2, wherein the position adjusting unit adjusts the displacement of the spatial coordinate position, using alignment information indicating an amount of displacement of a corneal apex of the subject's eye with respect to an apparatus body of the optical coherence tomography device in the two-dimensional tomographic images.

5. The anterior segment three-dimensional image processing apparatus according to claim 1, wherein the true circle calculating unit calculates the reference true circle having a diameter equal to a distance between the two SS positions identified using one of the representative images, from among the at least three SS positions identified by the first SS position specifying unit.

6. The anterior segment three-dimensional image processing apparatus according to claim 1, wherein the first SS position specifying unit detects from the representative images a sclera-uveal edge line showing a boundary between a sclera and a uvea in the subject's eye and a cornea posterior surface edge line showing a corneal posterior surface of the subject's eye, and identifies an intersection between the detected sclera-uveal edge line and corneal posterior surface edge line, as the SS position.

7. A non-transitory, tangible computer-readable recording medium that stores a program for causing a computer to function as:

a first SS position specifying unit that accepts identification of at least three SS positions indicating a spatial coordinate position of a scleral spur of a subject's eye, using at least two representative images from among a plurality of two-dimensional tomographic images constituting an anterior segment three-dimensional image of the subject's eye;

a true circle calculating unit that calculates a reference true circle passing through the at least three SS positions of the SS positions identified by the first SS position specifying unit in the anterior segment three-dimensional image; and a second SS position specifying unit that identifies the SS positions in non-representative images other than the representative images from among the plurality of two-dimensional tomographic images, based on the reference true circle calculated by the true circle calculating unit.

8. An anterior segment three-dimensional image processing method for processing an anterior segment three-dimensional image of a subject's eye by means of an optical coherence tomography device, the method comprising:

a determination step in which whether or not there is a displacement of a spatial coordinate position is determined based on two-dimensional tomographic images that constitute the anterior segment three-dimensional image;

a first SS position specifying step in which identification of at least three SS positions indicating a spatial coordinate position of a scleral spur of the subject's eye is accepted using at least two representative images from among the two-dimensional tomographic images;

a true circle calculating step in which a reference true circle is calculated that passes through the at least three SS positions identified in the first SS position specifying step in the anterior segment three-dimensional image; and a second SS position specifying step in which the SS positions in non-representative images other than the representative images from among the two-dimensional tomographic images of respective slice planes constituting the anterior segment three-dimensional image, are identified based on the reference true circle calculated in the true circle calculating step.

9. The anterior segment three-dimensional image processing apparatus according to claim 1, wherein the first SS position specifying unit comprises:

a candidate extracting unit that, for the at least two representative images, extracts a candidate edge line that is a candidate for a sclera-uveal edge line showing a boundary between a sclera and a uvea in the anterior segment from a predetermined region of each representative image;

a specifying unit that identifies the sclera-uveal edge line, based on brightness gradient information of the candidate edge line that has been extracted by the candidate extracting unit; and a corneal posterior surface edge line detecting unit that detects a corneal posterior surface edge line showing a corneal posterior surface of the anterior segment in the two-dimensional tomographic image, and identifies an intersection of sclera-uveal edge line identified by the specifying unit and the corneal posterior surface edge line detected by the corneal posterior surface edge line detecting unit, as the SS position.

10. The anterior segment three-dimensional image processing apparatus according to claim 9, further comprising:

a corneal posterior surface edge line detecting unit that detects a corneal posterior surface edge line showing a corneal posterior surface of the anterior segment in the two-dimensional tomographic image;

an iris anterior surface edge line detecting unit that detects an iris anterior surface edge line showing an iris anterior surface of an anterior segment in the two-dimensional tomographic image; and a region extracting unit that extracts the predetermined region based on the corneal posterior surface edge line detected by the corneal posterior surface edge line detecting unit and the iris anterior surface edge line detected by the iris anterior surface edge line detecting unit.

11. The anterior segment three-dimensional image processing apparatus according to claim 9, wherein the first SS position specifying unit identifies an inflection point of an edge line formed by connecting the sclera-uveal edge line identified by the specifying unit and the corneal posterior surface edge line detected by the corneal posterior surface edge line detecting unit, as the SS position.

12. The anterior segment three-dimensional image processing apparatus according to claim 9, wherein the first SS position specifying unit identifies the SS position based on brightness gradient information of an edge line formed by connecting the sclera-uveal edge line identified by the specifying unit and the corneal posterior surface edge line detected by the corneal posterior surface edge line detecting unit.

13. The anterior segment three-dimensional image processing apparatus according to claim 9, further comprising an iris anterior surface edge line detecting unit that detects an iris anterior surface edge line showing an iris anterior surface of the anterior segment in the two-dimensional tomographic images, wherein the first SS position specifying unit identifies an intersection of the sclera-uveal edge line identified by the specifying unit, the corneal posterior surface edge line detected by the corneal posterior surface edge line detecting unit, and the iris anterior surface edge line detected by the iris anterior surface edge line detecting unit, as the SS position.

* * * * *

UNITED STATES PATENT AND TRADEMARK OFFICE

CERTIFICATE OF CORRECTION

PATENT NO. : 9,265,411 B2
APPLICATION NO. : 14/499062
DATED : February 23, 2016
INVENTOR(S) : Jinji Chen et al.

It is certified that error appears in the above-identified patent and that said Letters Patent is hereby corrected as shown below:

Title Page

Item (72) the inventor whose name reads "Okamoto Keiichiro" should read --Keiichiro Okamoto--.

Signed and Sealed this
Twenty-sixth Day of July, 2016

Michelle K. Lee

Michelle K. Lee
*Director of the United States Patent and Trademark Office*